United States Patent [19]
Uomori et al.

[11] Patent Number: 5,357,293
[45] Date of Patent: Oct. 18, 1994

[54] APPARATUS FOR ANALYZING DEPTH PERCEPTION

[75] Inventors: Kenya Uomori; Mitsuho Yamada, both of Kyoto, Japan

[73] Assignee: ATR Auditory and Visual Perception Research Laboratories, Kyoto, Japan

[21] Appl. No.: 29,481

[22] Filed: Mar. 11, 1993

[30] Foreign Application Priority Data

Sep. 29, 1992 [JP] Japan .................................. 4-259461

[51] Int. Cl.$^5$ .............................................. A61B 3/14
[52] U.S. Cl. .................................. 351/209; 351/201; 351/210; 351/211
[58] Field of Search ............... 351/200, 201, 202, 209, 351/210, 211, 246

[56] References Cited

U.S. PATENT DOCUMENTS

| | | | |
|---|---|---|---|
| 2,168,308 | 8/1939 | Ames, Jr. ............................ | 351/201 |
| 2,340,856 | 2/1944 | Ames, Jr. ............................ | 351/201 |
| 3,984,156 | 10/1976 | Jernigan ............................. | 351/210 |
| 4,613,219 | 9/1986 | Vogel ................................. | 351/209 |
| 4,729,652 | 3/1988 | Effert ................................. | 351/210 |
| 4,838,681 | 6/1989 | Pavlidis .............................. | 351/210 |
| 5,212,506 | 5/1993 | Yoshimatsu et al. ................ | 351/210 |

FOREIGN PATENT DOCUMENTS

| | | | |
|---|---|---|---|
| 0125808 | 11/1984 | European Pat. Off. ............ | 351/210 |
| 2437819 | 6/1980 | France ............................... | 351/201 |
| -250657 | 10/1987 | German Democratic Rep. ................................. | 351/201 |
| 0625687 | 8/1978 | U.S.S.R. ............................. | 351/209 |

OTHER PUBLICATIONS

"Depth Perception with Random-dot Stereograms Under Dihcopotic-Sequential Presentation", by Takao Sato, Transactions of Institute of Electronics Information and Communication Engineers of Japan, MBE 88-188, pp. 193-198, Mar. 15, 1989.

*Primary Examiner*—Richard A. Bertsch
*Assistant Examiner*—Howard R. Richman
*Attorney, Agent, or Firm*—Lowe, Price, LeBlanc & Becker

[57] ABSTRACT

An image at a distant point and an image at a close point for generating depth perception of a subject are displayed on an image display monitor, and eye movement of the subject at that time is detected by an eye movement detecting portion. A calculating portion removes saccade component by using velocity or acceleration of the detected eye movement and calculates amplitude of vergence eye movement, change in convergence angle and cross-correlation of velocity or acceleration of the left and right eye movement to determine depth perception of the subject.

6 Claims, 15 Drawing Sheets

CONVERGENCE ANGLE

VELOCITY COMPONENT OF CONVERGENCE ANGLE

ACCELERATION COMPONENT OF CONVERGENCE ANGLE

F I G. 1 3 (a)
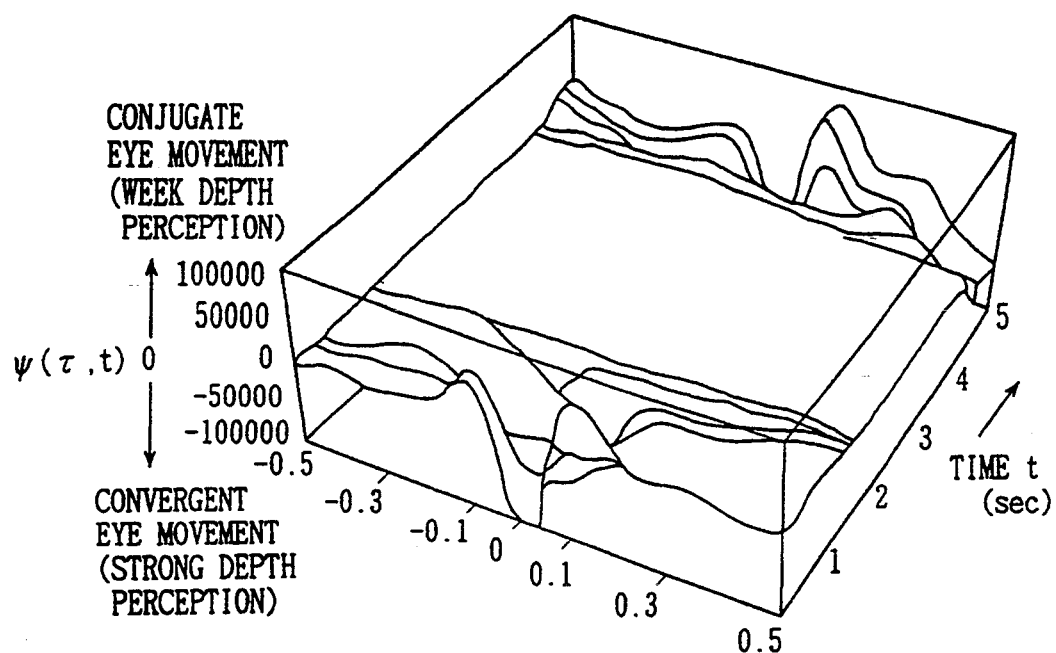
F I G. 1 3 (b)
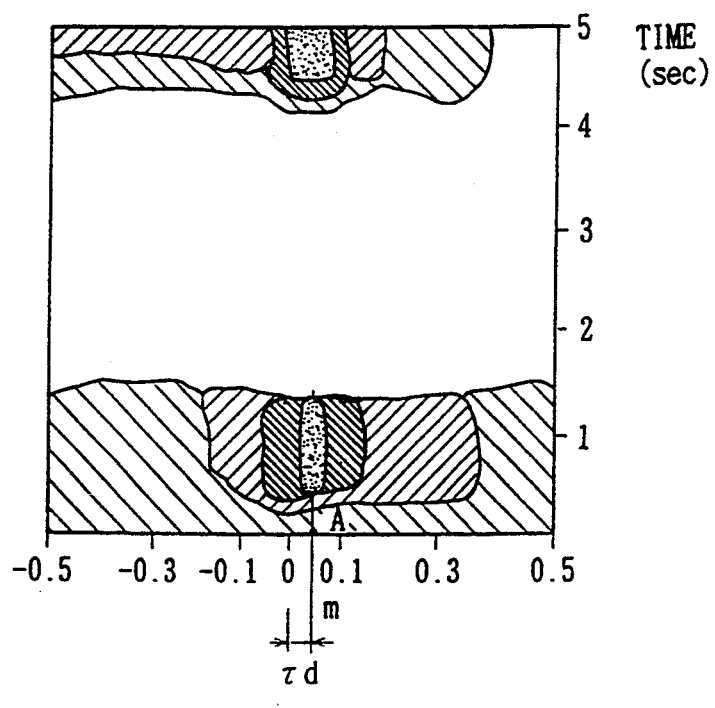

X Y Z COORDINATE SYSTEM

POLE COORDINATE SYSTEM

APPARATUS FOR ANALYZING DEPTH PERCEPTION

BACKGROUND OF THE INVENTION

1. Field of the Invention

The present invention relates to an apparatus for analyzing depth perception. More specifically, the present invention relates to an apparatus for analyzing depth perception of a subject for evaluating a stereoscopic image.

2. Description of the Background Art

Generally, the sense of depth of stereoscopic images have been evaluated subjectively. One such example is described in "Depth Perception with Random-dot Stereograms under Dihcoptic-Sequential Presentation", Transactions of Institute of Electronics Information and Communication Engineers of Japan, MBE 88-188, pp. 193-198 by Sato.

This article reports results of binocular stereopsis experiment by dihcoptic stimulation. More specifically, in the experiment, a random dot pattern of 3×3 pixels is displayed on a color CRT, the central portion of the random dot pattern is moved as a target to provide disparity, the duration of presentation is changed, and the subject is asked for a determination as to whether the target is in front of or behind the background.

However, the method disclosed in this article evaluates or measure the sense of depth of the subject by a psychophysical manner which requires several ten times of repeated trial per one condition. If the method of measurement is not appropriately set, subjective determination of the subject himself affects the measurement itself. In addition, since a large number of calculations are necessary to obtain the results of measurement, real time measurement is difficult.

SUMMARY OF THE INVENTION

Therefore, an object of the present invention is to provide an apparatus for analyzing depth perception which can measure depth perception of a subject in an objective manner at real time so that the result of measurement can be utilized for evaluating stereoscopic images.

Briefly stated, in the present invention, eye movement of a subject while the subject is gazing at a target for depth perception is detected, saccade component is removed, only a vergence eye movement is extracted by using velocity or acceleration of the eye movement, and the depth perception of the subject is determined by calculation of amplitude of the vergence eye movement, change in the convergence angle, and of cross-correlation of velocity or acceleration of left and right eye movement.

Therefore, according to the present invention, the depth perception can be objectively evaluated in real time, and it can be used for evaluation of stereoscopic images.

According to a preferred embodiment of the present invention, head movement of the subject is detected, and in response to the detected head movement and eye movement, amplitude of vergence eye movement, change in the convergence angle, cross-correlation of acceleration and velocity of left and right eye movement are calculated to determine depth perception of the subject.

Therefore, according to the preferred embodiment of the present invention, general determination of depth perception of the subject can be realized on the basis of the head and eye movements of the subject.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 13(a-b) shows an example of measurement of cross-correlation $\psi(\tau)$.

DESCRIPTION OF THE PREFERRED EMBODIMENTS

Figure 1:
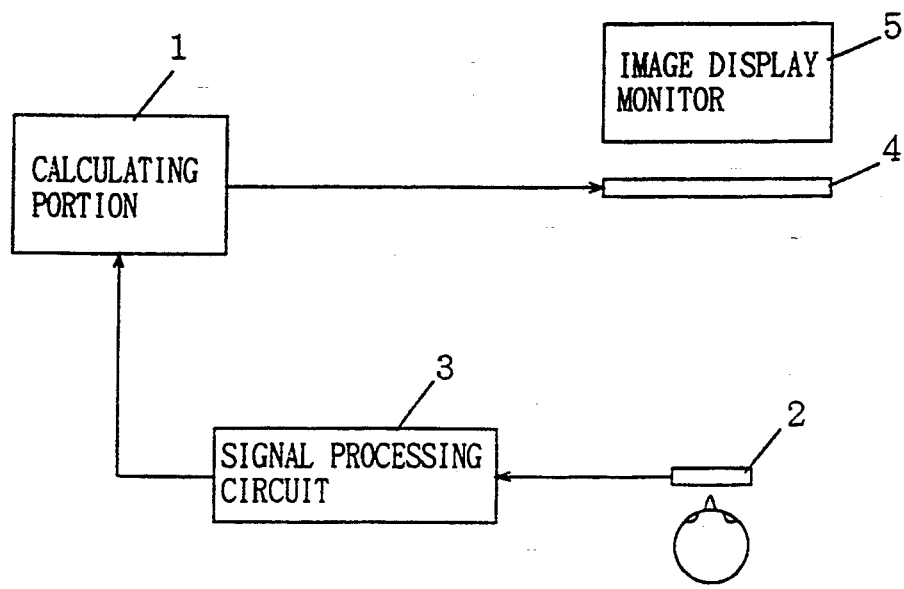
FIG. 1 is a block diagram of one embodiment of the present invention.

FIG. 1 is a block diagram of one embodiment of the present invention. Referring to FIG. 1, in order to detect movement of both eyes of the subject, an eye movement detecting portion 2 is provided, the detection output of which is applied to a signal processing circuit 3 to be processed, and eye movement data is applied to a calculating portion 1. A board 4 for calibration is provided in front of the subject. The board 4 for calibration calibrates the eye movement detecting portion 2. An image display monitor 5 is provided behind the board 4 for calibration. The image display monitor 5 displays an image at a distant point and an image at a close point to the subject. The calculating portion 1 analyzes the eye movement data detected by the eye movement detecting portion 2 when the subject moves his or her line-of-sight from the image at the distant point to the image at the close point on the image display monitor 5, and determines depth perception of the subject.

Figure 2:
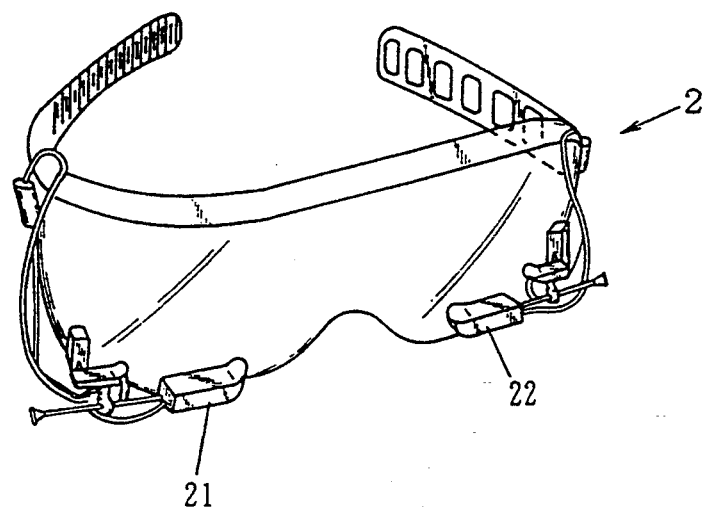
FIG. 2 shows an example showing the eye movement detecting portion shown in FIG. 1 attached to goggles.
Figure 3:
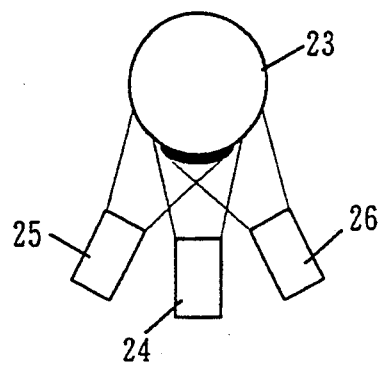
FIG. 3(a-c) shows a specific example of the eye movement detecting portion.
Figure 3:
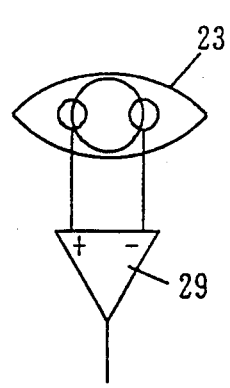
Figure 3:
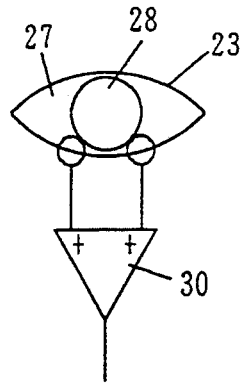

FIG. 2 shows an example in which the eye movement detecting portion shown in FIG. 1 is attached to goggles, and FIG. 3 shows a specific example of the eye movement detecting portion.

The eye movement detecting portion 2 shown in FIG. 1 is attached to goggles as shown in FIG. 2, and subject wears the goggles. The eye movement detecting portion 2 utilizes limbus reflection method and includes detecting portions 21 and 22 for detecting movements of left and right eyes. The detecting portions 21 and 22 each include a light emitting diode 24 provided centered with respect to the eyeball 23 and photodiodes 25 and 26 provided on both sides of the diode 24 as shown in FIG. 3(a). A light emitting diode radiating infrared rays having relatively wide directivity of about ±21° is used as the light emitting diode 24, while ones having acute directivity of about ±10° are used as the photodiodes 25 and 26. The light beam emitted from the light emitting diode 24 to the eyeball 23 is reflected from the iris of the eye 28 and from the white of the eye 27 with different reflectivity, and the difference in reflectivity is amplified by an operational amplifier 29. If the difference is calculated, a horizontal output (left and right) is obtained as shown in FIG. 3(b), and if the sum is calculated by an operation amplifier 30, a vertical (up and down) output is obtained as shown in FIG. 3(c). The eye movement detecting portion 2 may utilize a contact lens or a TV camera other than aforementioned limbus reflection method.

Figure 4:
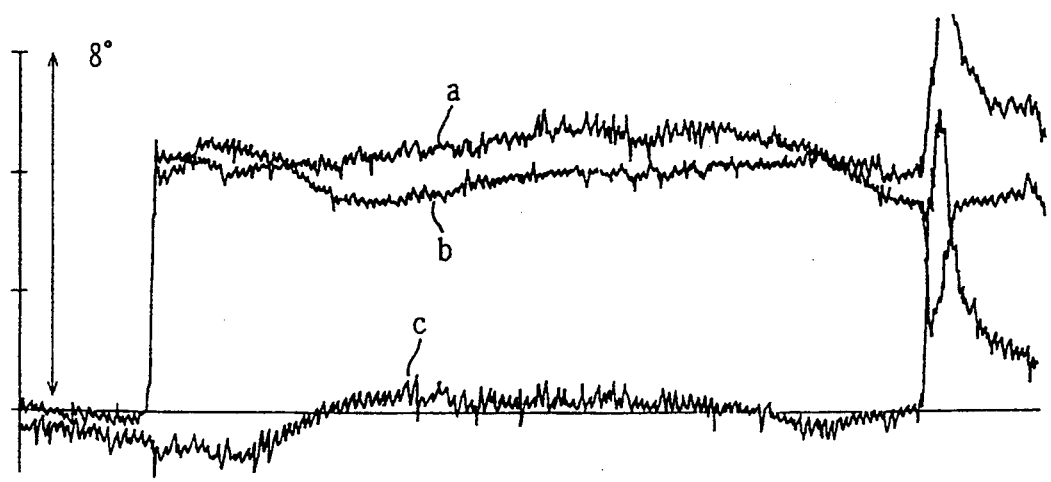
FIG. 4 shows an example of eye movement data detected by the eye movement detecting portion.
Figure 5:
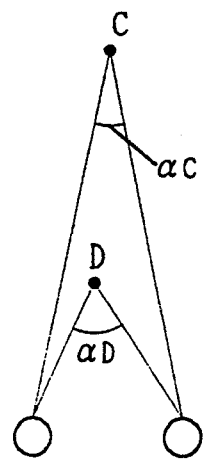
FIG. 5 illustrates convergence angle.
Figure 6:
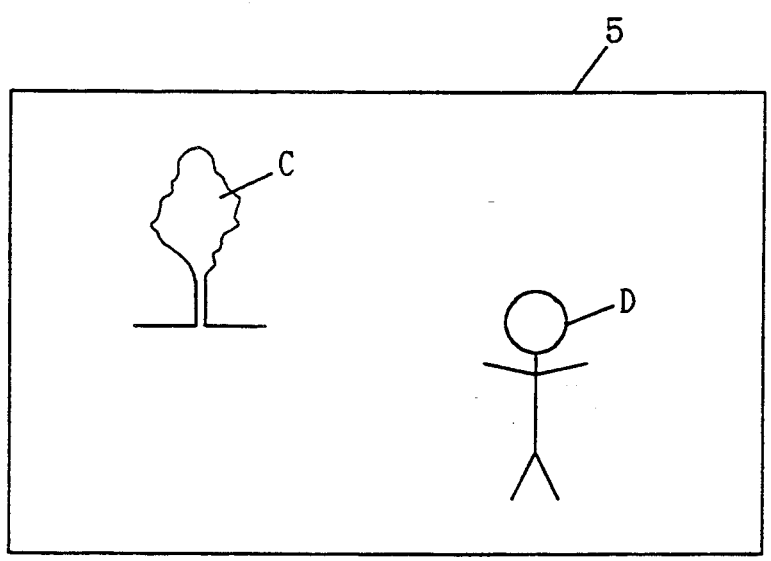
FIG. 6 shows an example of the image displayed on the image display monitor shown in FIG. 1.

FIG. 4 shows an example of the eye movement data detected by the eye movement detecting portion, FIG. 5 shows the convergence angle, and FIG. 6 shows an example of the image displayed on the image display monitor shown in FIG. 1.

An image C at a distant point and an image D at a close point are displayed on the image display monitor 5 as shown in FIG. 6, and the eye movement data detected by the eye movement detecting portion 2 when the subject moves his or her line-of-sight from the image C at a distant point to the image D at a close point is as shown in FIG. 4. In FIG. 4, the reference character a represents the movement of the left eye in the horizontal direction Xeye-L, b represents the movement of the right eye Xeye-R, and c represents the convergence angle.

The convergence angle means the angle of the line-of-sight of the left eye minus the angle of the line-of-sight of the right eye. When the subject gazes at the image C at the distant point, the convergence angle is $\alpha_c$ and when the subject gazes at the image D at the close point, the convergence angle is $\alpha_D$, as shown in FIG. 5. As is apparent from FIG. 5, the convergence angle $\alpha_D$ when the subject gazes at the image D at a close point is large, while the convergence angle $\alpha_c$ when the subject gazes at the image C at a distant point is smaller. In other words, the movement of the line-of-sight in the depth direction can be represented by the change in the convergence angle. Again referring to the change in the convergence angle of FIG. 4, the line-of-sight of the subject moves on the surface of the image display monitor 5 and the viewing distance hardly changes. However, the convergence angle is increased when the subject looks at the image D at a close point on the screen. The change in the convergence angle is generated in this manner when the subject looks at images providing sense of depth. The eye movement accompanying such change in the convergence angle is referred to as vergence eye movement. In this movement, the left and right eyes move in opposite directions. However, the change in the convergence angle is inherently the eye movement induced when the subject feels the sense of depth. When the subject gazes the image display monitor 5 for a little longer, the subject recognizes that the viewing distance is not changed, since he or she is gazing merely at the surface of the image display monitor 5, and the convergence angle returns to the initial state. Therefore, if such a change in the convergence angle is generated, that is, when vergence eye movement is generated, it is supposed that there is a depth perception (the subject feels the sense of depth).

Figure 7:
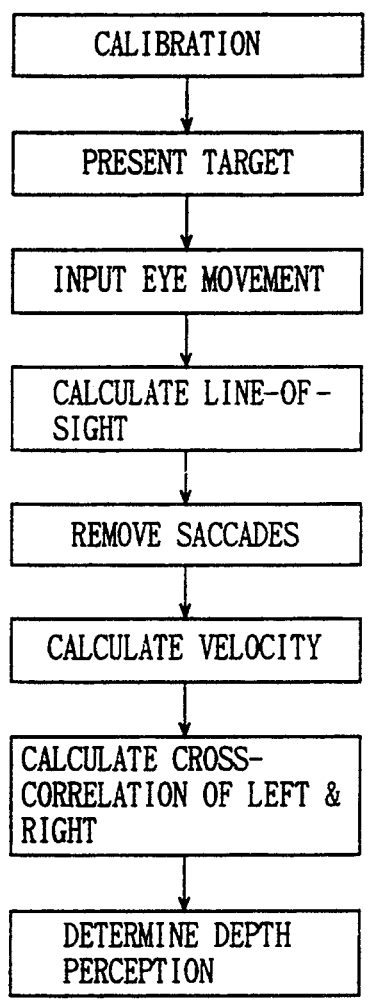
FIG. 7 is a flow chart showing the operation of one embodiment of the present invention.
Figure 8:
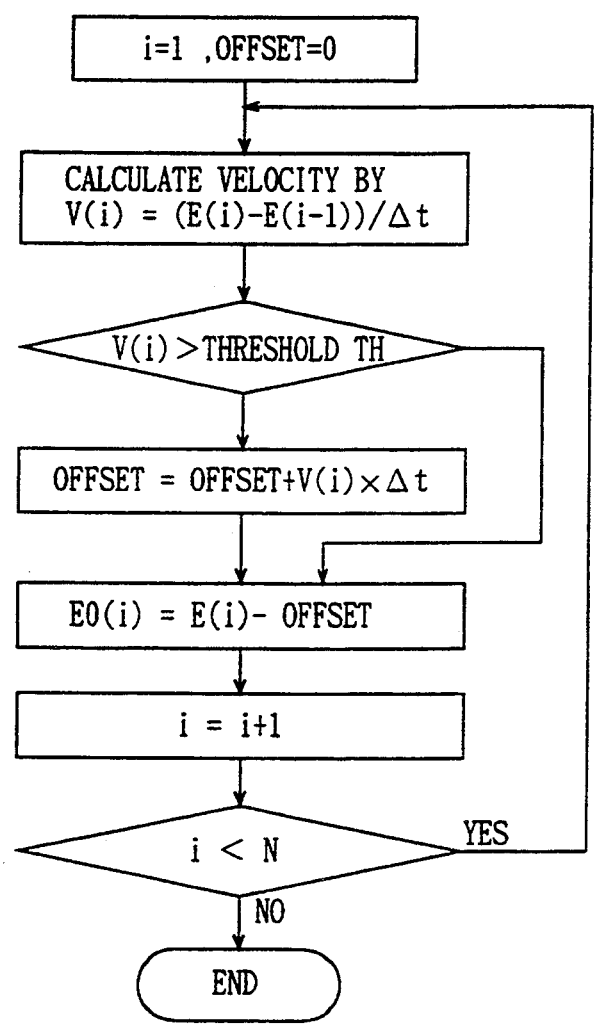
FIG. 8 is a more specific flow chart of the step of removing saccades shown in FIG. 7.
Figure 9:
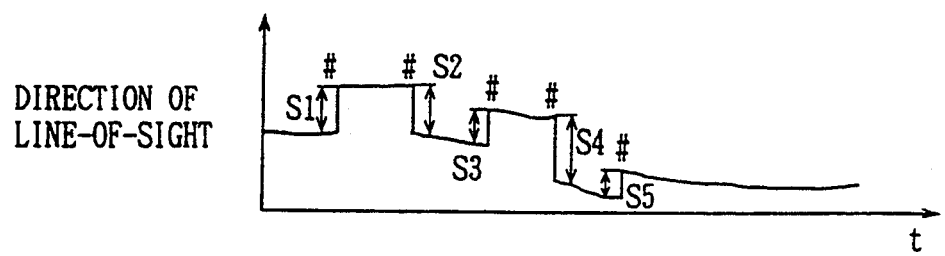
FIG. 9(a-b) shows a method of removing the saccades.
Figure 9:
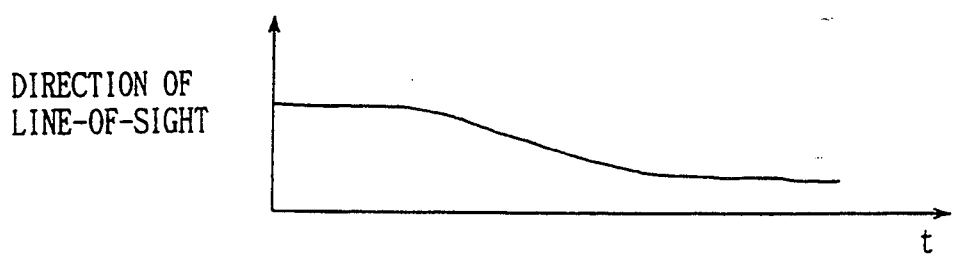
Figure 10:
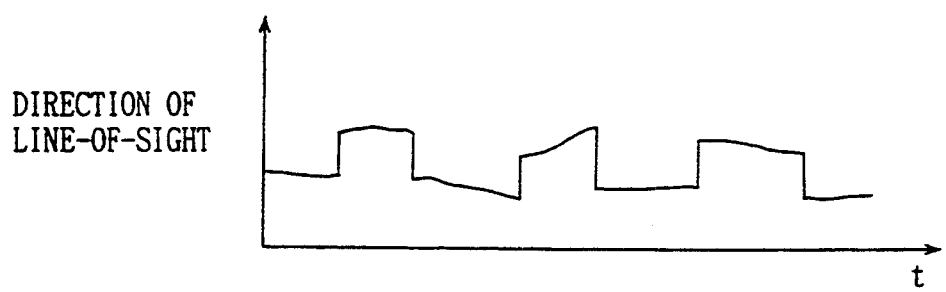
FIG. 10(a-c) shows the method of detecting saccades.
Figure 10:
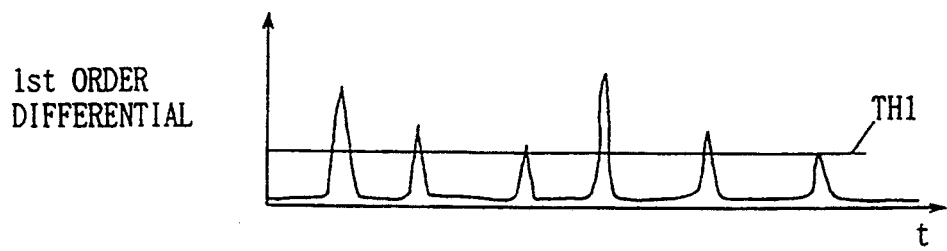
Figure 10:
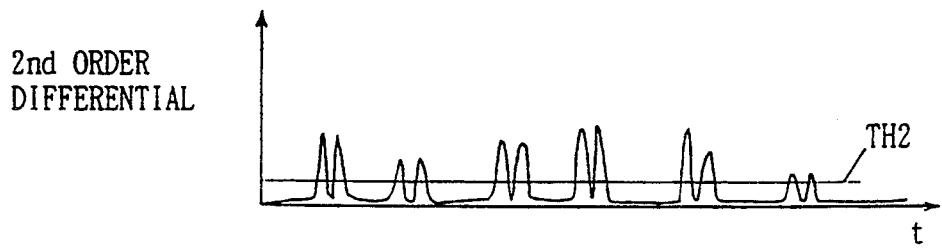

FIG. 7 is a flow chart showing the operation of one embodiment of the present invention, FIG. 8 is a more specific flow chart showing the step of removing saccades shown in FIG. 7, FIG. 9 shows the method of removing saccades, and FIG. 10 shows the method of detecting saccades.

Referring to FIGS. 7 to 10, operation of one embodiment of the present invention will be described in detail. First, as shown in FIG. 1, a board 4 for calibration is placed in front of the subject and calibration is carried out. In this calibration, the subject successively gazes at targets fixed on the board 4, the direction of the line-of-sight to which targets are known in advance. At this time, the calculating portion 1 calculates a coefficient for converting the output from the signal processing circuit 3 to a position of the line-of-sight for calibration. When the calibration is completed, the board 4 for calibration is removed, and the image C at a distant point and the image D of a close point such as shown in FIG. 6 are displayed on the image display monitor 5. The eye movement when the subject moves his line-of-sight from the image C at the distant point to the image D at the close point is detected by the eye movement detecting portion 2, and eye movement data is input through signal processing circuit 3 to calculating portion 1. The calculating portion 1 calculates the line-of-sight on the basis of the eye movement data and then removes saccades.

The eye movement can be divided into a high speed skipping eye movement generally called saccade, a relatively slow vergence eye movement and a following eye movement (smooth movement which occurs when the line-of-sight follows an object). Generally, the actual eye movement is a mixture of these three types of movements as shown in FIG. 9(a). In FIG. 9(a), the reference character # represents a saccade. In order to determine depth perception, the saccade component must be removed. There are two methods of removal. That is, ① since saccades are generally generated to have the same amplitude in left and right directions, the convergence angle which is the difference in the angle of the line-of-sight of the left and right eyes is calculated and change therein is measured. ② since the saccades occur sometimes in asymmetry in left and right directions, the saccade component is removed from the result of measurement of eye movement of left and right eyes respectively, convergence angle is calculated thereafter, and the change in the convergence angle is determined. The former method requires simple calculation, that is, the angle of line-of-sight of the right eye minus the angle of the line-of-sight of the left eye. In the latter method, velocity or acceleration of the eye movement is calculated at first for removing saccade.

The method of removing saccades will be described in detail with reference to FIGS. 8 to 10. The calculating portion 1 sets the time i to 1, and sets the offset to 0. Then, the calculating portion 1 calculates the velocity V (i) by the following equation.

$$V(i) = (E(i) - E(i-1))/\Delta t \tag{1}$$

Here E (i) represents the angle in the direction of the line-of-sight. Δt is a time between i and i−1(=1). The calculating portion 1 determines whether or not the velocity V (i) is larger than a threshold value TH. If the velocity V (i) is larger than the threshold value TH, it is determined that the saccade is generated as shown in FIG. 10(b), the V(i).Δt is added to the offset value to calculate the magnitude of saccade, and the saccade is subtracted from the angle E (i) of the direction of the line-of-sight. Then, 1 is added to time i. If the time i is not larger than n, the above described operation is repeated until the time i reaches n. It may be determined that the saccade is generated when the acceleration is larger than a certain threshold value TH2 as shown in FIG. 10(c).

In the example shown in FIG. 8, difference between adjacent data in time sequence data of the eye movement is calculated and when this difference is larger than the threshold value TH, it is determined that the saccade is generated. The offset in accumulated value of the saccade component from the time i=0 is calculated, and by subtracting the magnitudes S1 to S5 of the saccades from the measured data V (i) shown in FIG. 9(a), the waveform of the eye movement with the saccades removed such as shown in FIG. 9(b) can be obtained. After such processing, subtraction of the angles of left and right line-of-sight is effected to provide time change of the convergence angle.

As described above, by either of the above described two methods, time change of the convergence angle is obtained, and based on this, amplitude and change (differential value) thereof are calculated to analyze whether there is vergence eye movement generated.

Figure 11:
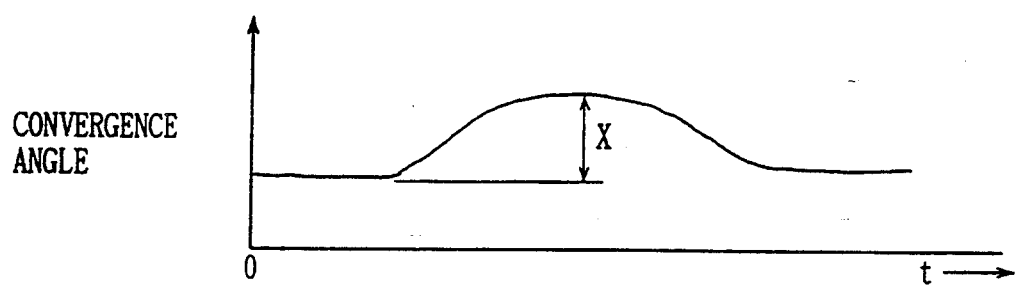
FIG. 11(a-c) is a diagram of waveforms for explaining generation or non-generation of depth perception.
Figure 11:
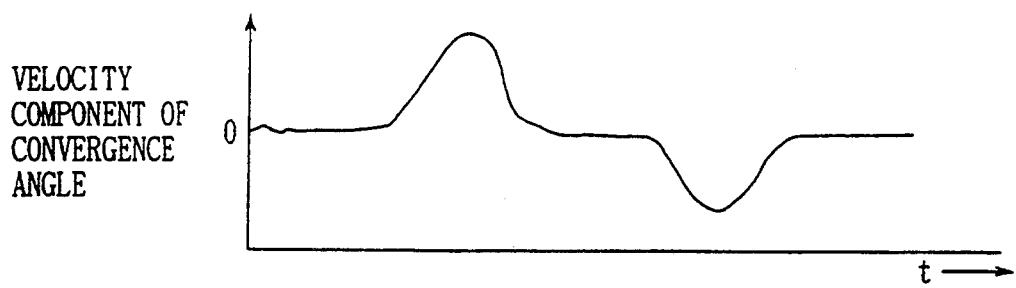
Figure 11:
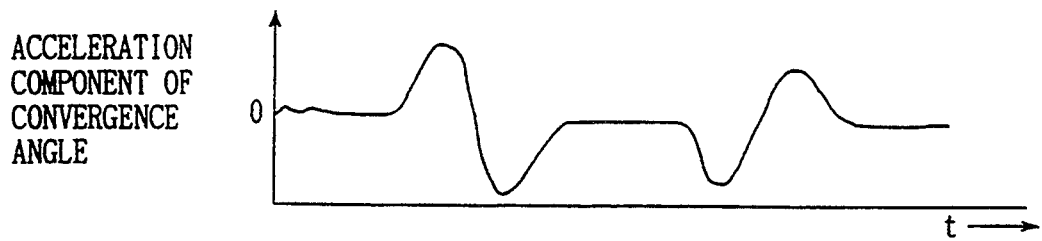

FIG. 11 is a diagram of waveforms showing generation or non-generation of depth perception. As shown in FIG. 11(a), if the subject starts gazing at the image D at the close point shown in FIG. 6 at time t=0, the convergence angle increases after the lapse of a prescribed time period and resumes to the original state thereafter. By measuring the amplitude of the convergence angle (difference between the maximum value and the value before the start of movement of the line-of-sight) X, determination as to whether the depth perception is generated is carried out based on this value. If the absolute value of X is larger that a certain threshold value, it is determined that there is generated depth perception. The standard deviation or variance of the data of change of the convergence angle may be calculated to determine the generation of the depth perception if such value is large. Alternatively, the velocity (first order differential) of the time change data of the convergence angle shown in FIG. 11(b) or acceleration (second order differential) shown in FIG. 11(c) may be calculated. Using the absolute value of the maximum value, the standard deviation or variance of the velocity or of the acceleration, generation of depth perception may be determined based on whether such value is larger than a certain threshold value.

In order to determine whether depth perception is generated or not when the subject is looking at a motion picture, the following method is available. More specifically, whether a movement such as vergence eye movement in which left and right eyes move in opposite directions is generated and there is depth perception, or a movement such as following eye movement in which left and right eyes move in the same direction is generated and the subject does not recognize an object moving in the depth direction can be determined. As a method of measurement, the direction of the light-of-sight of the eyeballs or the first order differential (velocity) or the second order differential (acceleration) with respect to the time thereof is calculated, the time change thereof is plotted on a graph and by determining whether the movement of the left and right eyes are in opposite directions or in the same direction, whether or not there is the depth perception can be determined.

As for the method of measuring generation of vergence eye movement (related to generation of depth perception) and generation of conjugate eye movement (depth perception is not generated: related to simple two dimensional movement), there is a method of measuring cross correlation of velocity and acceleration of left and right eyes. If the image shown in FIG. 6 is a motion picture, three types of eye movements, that is, saccade, vergence eye movement and following eye movement mentioned above are generated. At first, by using the above mentioned method, the difference between the angle of the line-of-sight of the left and right eyes or the saccade of respective eye movement is removed, and then the convergence angle is calculated. Thereafter, velocity (first order differential) or acceleration component (second order differential) of the angle of the line-of-sight of the left and right eyes is calculated respectively, and cross-correlation therebetween is calculated. The equation for calculating the cross correlation at time t=t0 is represented as $$\psi(\tau) = (2N + 1)^{-1} \sum_{i=-N}^{N} R(ti)L(ti + \tau)$$

where 2N+1 represents the number of samples of the eye movement for the time period to be measured, and i=−N to N.

Figure 12:
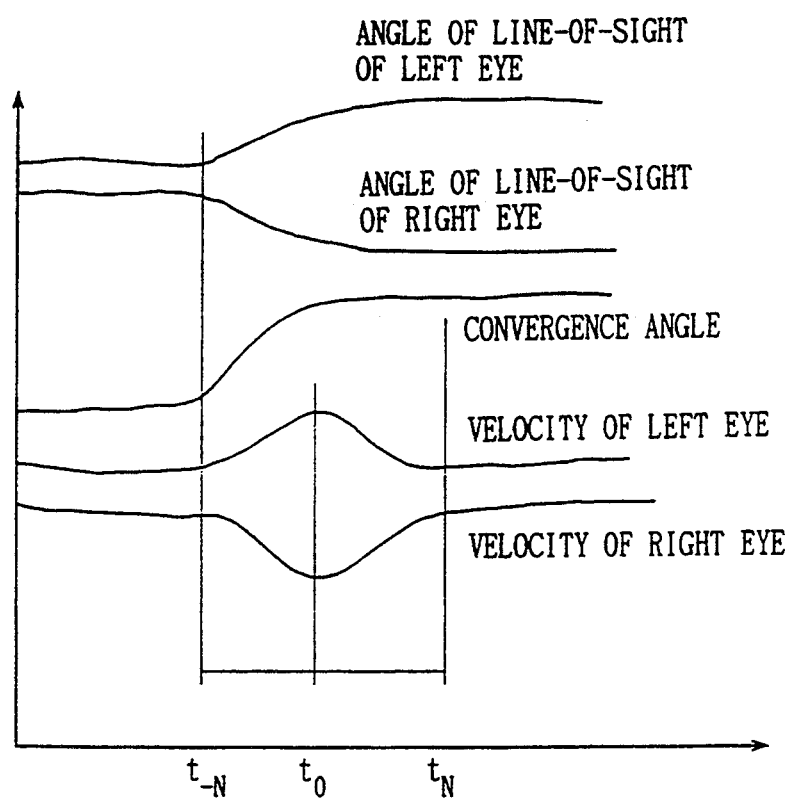
FIG. 12 shows a method of sampling the eye movement.

FIG. 12 shows a method of sampling the eye movement. With respect to τ, in the above equation, the cross correlation ψ(τ) is calculated for preset values −τ1 to τ1. In addition, the change of the cross-correlation ψτ is calculated with the position of t0 being changed. R and L represent velocity or acceleration in the direction of the line-of-sight of the right and left eyes, respectively.

In this example, if vergence eye movement occurs, the value of the cross correlation ψ has a negative value, and if the reaction is larger, the absolute value becomes larger. This has a positive correlation with the degree of the generated depth perception. More specifically, it means that strong depth perception is generated when the cross-correlation ψ is large in the negative direction. When both eyes move in the same direction (generally referred to as general conjugate eye movement) such as in the case of following eye movement, the cross-correlation ψ has a positive value. This means that the depth perception is not much generated and the subject has simple two dimensional recognition.

FIG. 13 shows an example of measurement of the cross-correlation – ($\tau$). FIG. 13 shows an example of measurement of the cross-correlation of angular velocity in the direction of the line-of-sight when the subject moves his line-of-sight in the depth direction from a distant point at the viewing distance of 1000 mm to a close point of 300 mm. The subject moves his or her attention to the close point from the time 0.5 sec. FIG. 13(a) is a three dimensional plotting of relations between each of $\tau$, time t and the cross-correlation function $\psi$, and FIG. 13 (b) represents the cross-correlation function $\psi$ in positive direction by white, and in negative direction by black. As is apparent from FIG. 13, the degree of generated depth perception (how much the eye balls move in the vergence direction) can be treated quantitatively by continuous amount. More specifically, it is understood that strong depth perception is generated at the time represented by black in FIG. 13(b). Alternatively, portions having values smaller than a certain threshold value of the cross-correlation $\psi$ may be extracted which portions correspond to strong depth perception. By the first 1.5 sec, the reaction ends, thereafter the eyeballs gaze approximately at one point, and after 4 sec, the waveforms change again, which means that the subject moves his or her line-of-sight in another direction.

The data in the $\tau$ axis is effective to determine quantitatively by continuous amount whether the eyeballs react in the vergence direction or in the direction of conjugate eye movement when reaction of left and right eyes are not simultaneously, that is, when there is a time difference between the movements of the left and right eyes by some influence. If calculation is done only for the case of $\tau=0$, the black portion moves in parallel to the direction of $\tau$ when there is a time difference between the reactions of both eyes, making evaluation impossible.

Further, by utilizing the data, effect of dominant eye (which of the eyes react first) can be determined. When we draw a center line m at the black portion of FIG. 13(b) (the portion where vergence eye movement is generated, that is, where there is generated depth perception), an intersection A of the center line m and the $\tau$ axis represents the time deviation $\tau$d of the reaction of both eyes. Referring to FIG. 13(b), the reaction of the left eye is delayed by 0.05 sec. Namely, the right eye reacts first and the dominant eye determined in terms of the quick reaction is the right eye. It is considered that the magnitude of time deviation $\tau$d is related to the dominance of the eye, and therefore if the absolute value of the time deviation $\tau$d is larger, the effect of dominant eye is stronger.

Figure 14A:
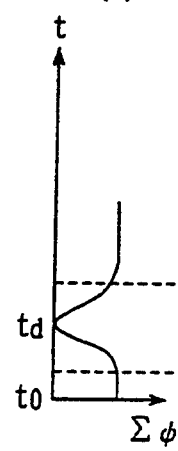
FIG. 14(a-c) shows a method of determining a line m of FIG. 13.
Figure 14B:
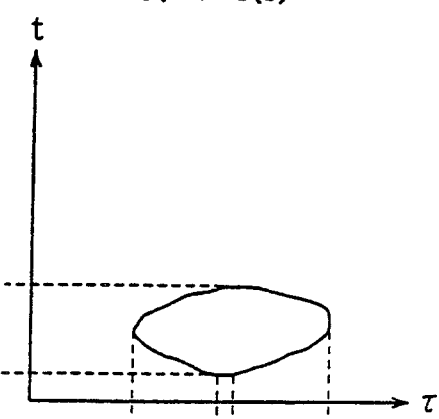
Figure 14C:
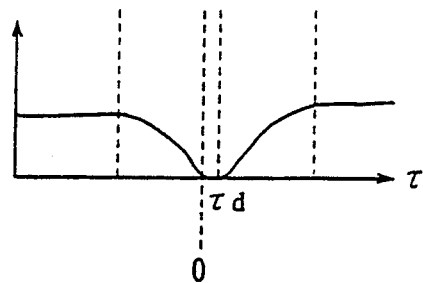

FIG. 14 shows a method of determining the line m of FIG. 13. The graph of FIG. 14(b) is a schematic representation of FIG. 13(b), FIG. 14(c) shows integration of the cross-correlation $\psi$ with respect to t for each $\tau$ value, and FIG. 14(a) shows integration of the cross-correlation $\psi$ with respect to $\tau$ for each t value. When a point at which the cross-correlation $\psi$ has the minimum value in the graph of FIG. 14(c) is assumed to be $\tau$d, the line m is determined. If the point at which the cross-correlation $\psi$ has the minimum value in the graph of FIG. 14(a) is assumed to be td, td represents the time at which both eyes start reaction in average, and therefore latency of the eye movement can be measured. Alternatively, a square well function such as shown in FIG. 14, for example, $\psi = B \times (\tau - \tau d)^2 + C$ ($\tau$d, B, C: constants) may be fitted to calculate $\tau$d, instead of using the minimum value. The same applies to td.

If it is previously known that the effect of dominant eye is not very strong, calculation may be carried out only for the case of $\tau=0$ for analysis. As described above, by this embodiment, strength of generated depth perception of the subject can be measured quantitatively.

Figure 15:
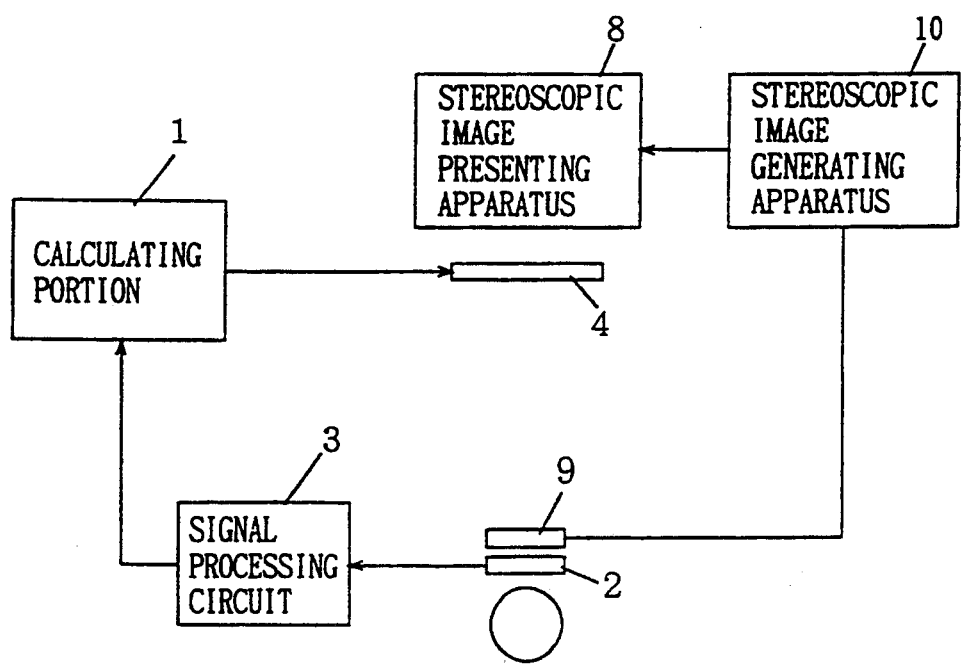
FIG. 15 is a block diagram of another embodiment of the present invention.

FIG. 15 is a block diagram showing another embodiment of the present invention. In the embodiment shown in FIG. 15, a stereoscopic image is displayed as a target to determine depth perception of the subject. Various methods are proposed to display a stereoscopic image. In the embodiment shown in FIG. 15, a stereoscopic image signal is generated by a stereoscopic image generating device 10 to display a stereoscopic image on a stereoscopic image presenting device 8, and the subject observes the stereoscopic image by means of liquid crystal shutter glasses 9 for observing the stereoscopic image.

Figure 16:
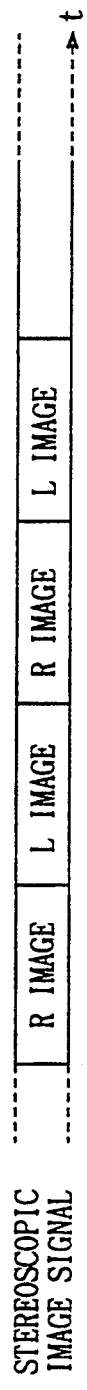
FIG. 16(a-c) is a timing chart for displaying a stereoscopic image.
Figure 16:
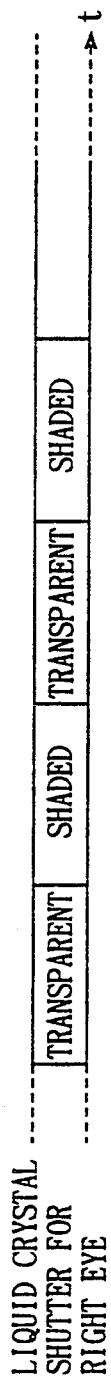
Figure 16:
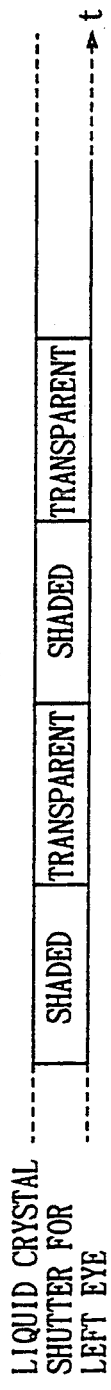

FIG. 16 is a timing chart for displaying a stereoscopic image. As shown in FIG. 16(a), a right (R) image and a left (L) image are alternatively displayed on stereoscopic image presenting device 8, and correspondingly, the liquid crystal shutter for right eye of the liquid crystal shutter glasses 9 is rendered transparent when the image for the right eye is displayed on the stereoscopic image displaying device 8 as shown in FIG. 16(b), while the liquid crystal shutter for the left eye is shaded as shown in FIG. 16(c). The left and right shutters are operated in the reverse manner when the image for the left eye is displayed. In this manner, the eye movement while the subject is gazing at the stereoscopic image is detected by the eye movement detecting portion 2, and depth perception is analyzed in the similar manner as in the above described embodiment. What is different in this embodiment is the method of forming a stereoscopic image. This will be described in the following.

Figure 17:
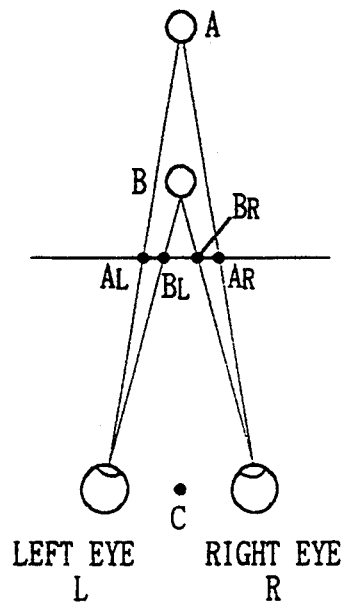
FIG. 17(a-b) is a diagram for explaining movement in the depth direction in a three dimensional space of a simple point.
Figure 17:
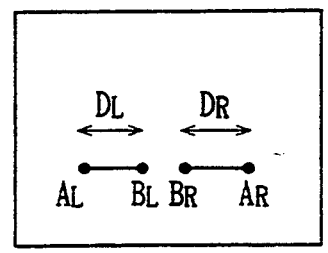
Figure 18:
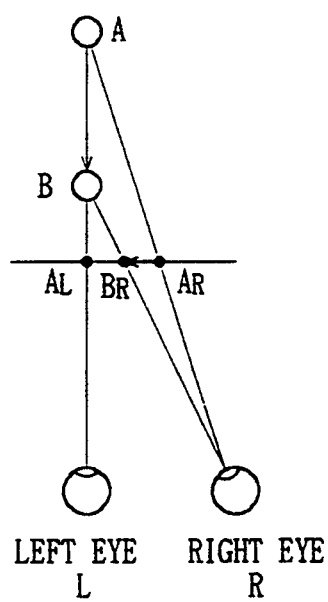
FIG. 18(a-b) shows movement in the depth direction when horizontal disparity is made 0.
Figure 18:
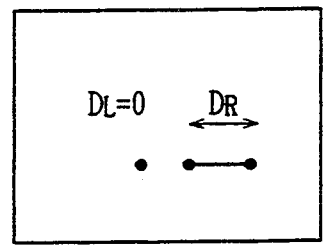

FIGS. 17 and 18 are diagrams for explaining the movement in the depth direction of a simple point in a three dimensional space. Referring to FIG. 17(a), the positions on the screen of the point images for left and right eyes respectively are shown by the mark ●, and the positions in the three dimensional space virtually perceived by these images are represented by the mark . Assume that a point is observed at the point A at first and the point moves to the point B. At this time, the movement of the display screen is as shown in FIG. 17(b), that is, respective points move in opposite directions by the same distance, where horizontal disparity of the left and right eyes is DR=DL. At this time, both eyes follow this point. However, because of the vergence eye movement, both eyes rotate inward. At this time, generally, vergence eye movement occurs accompanied with depth perception which is the sense of movement in the depth direction of the point. However, it is possible that although vergence eye movement occurs, it does not accompany depth perception. It cannot be ensured whether vergence eye movement accompanies depth perception only when there is a movement, that is, only when a motion picture is observed. In such a case, the result is that the vergence eye movement is simple following of the point. In this embodiment, when an object moving in the depth direction is to be followed by the eyes, only the vergence eye movement induced from the generation of depth perception is measured, which has an effect of reducing error in measurement of the depth perception.

In order to avoid the above described problem, in the method of providing movement of the stereoscopic image in the depth direction, one horizontal disparity is set to be, for example, DL=0 as shown in FIG. 18. In this case, the point is static for the left eye, and the movement of the-point is in the direction of the line-of-sight of the left eye. In FIG. 7, the point moves on a line connecting the center C between both eyes and the point A. In FIG. 18, the point moves on the line-of-sight of the left eye. However, the space between both eyes is about 6.5 cm and generally the viewing distance to the screen is set to be several meters or longer. Therefore, such difference is not a problem.

If the eye movement of both eyes is measured with such setting, movement of the left eye is not necessary in principle and therefore it is supposed that the right eye only moves and the vergence eye movement does not occur. However, if the change of disparity is as small as DR=about 1° is less, the left eye also reacts, though not symmetrical, and if there is depth perception, vergence eye movement occurs. If simple two dimensional movement only is recognized, that is, when the movement in the depth direction is not recognized, both eyes react in the same direction to provide conjugate eye movement.

By utilizing this fact, only the vergence eye movement with depth perception generated can be measured, not the simple movement of following the point in the depth direction. As for the method of analysis, the same method as described in the above embodiment can be used. More specifically, by measuring the change in the convergence angle after the removal of saccades, and by calculating cross-correlation of velocity or acceleration of the movement of both eyes, depth perception of the subject with respect to an object moving in the depth direction provided by a stereoscopic image can be quantitatively determined. Further, not only the point image but an image of a moving object may be displayed by means of a plurality of points, whereby depth perception of movement of an object which has volume in the depth direction can be determined.

As described above, by this embodiment, only the vergence eye movement induced by the generation of depth perception can be measured as interference by the following eye movement with the movement of an object in the depth direction can be reduced, and accordingly the strength of depth perception can be measured with high precision.

Figure 19:
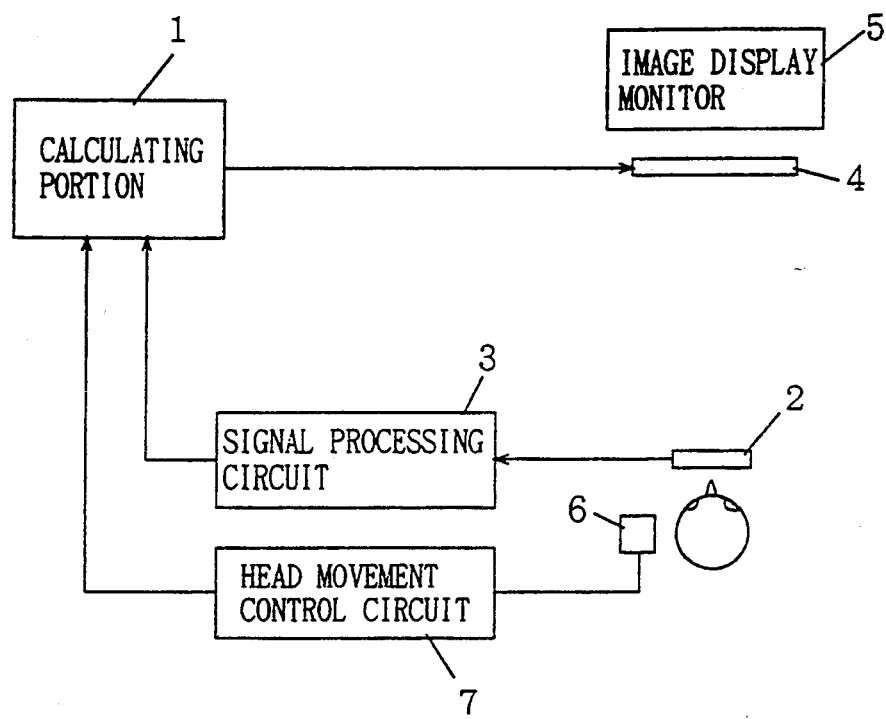
FIG. 19 is a block diagram showing a still further embodiment of the present invention.
Figure 20:
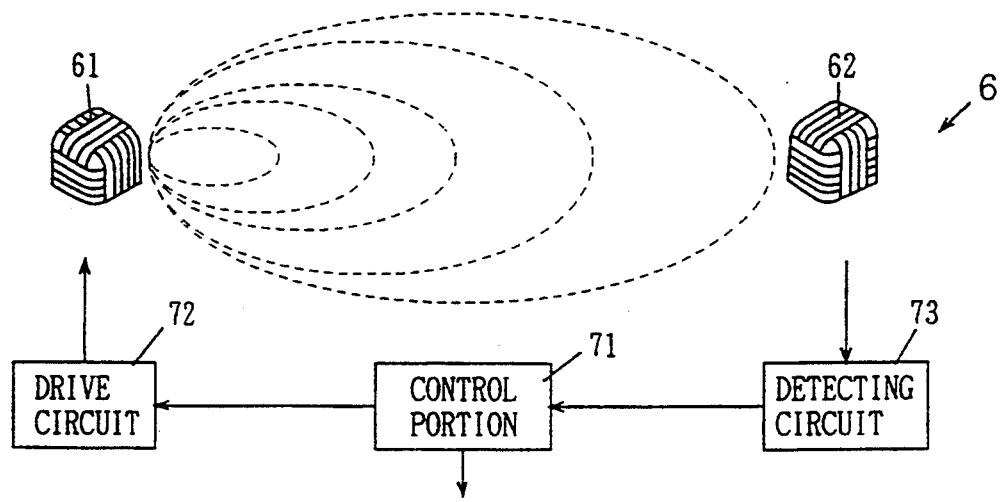
FIG. 20 shows an example of the head movement detecting portion shown in FIG. 19.

FIG. 19 is a block diagram showing a further embodiment of the present invention, and FIG. 20 shows a specific example of the head movement detecting portion shown in FIG. 19.

In the embodiment of FIG. 18, head movement of the subject is also detected. For this purpose, a head movement detecting portion 6 and a head movement control circuit 7 are provided. Except this point, the structure is the same as that shown in FIG. 1. The head movement detecting portion 6 includes an orthogonal coil serving as a source 61 and an orthogonal coil serving as a sensor 62 as shown in FIG. 19. The head movement control circuit 7 includes a control portion 71, a drive circuit 72 and a detecting circuit 73. The drive circuit 72 drives the orthogonal coil of the source 61 to generate a magnetic field in response to an instruction from the control portion 71. When the subject wearing the head movement detecting portion 6 moves, a voltage is induced in the sensor 62, the voltage is detected by the detecting circuit 73 and the detected output is calculated by the control portion 71, so that data corresponding to the movement of the head is output. The head movement detecting portion 6 is attached to the goggles shown in FIG. 2.

Figure 21:
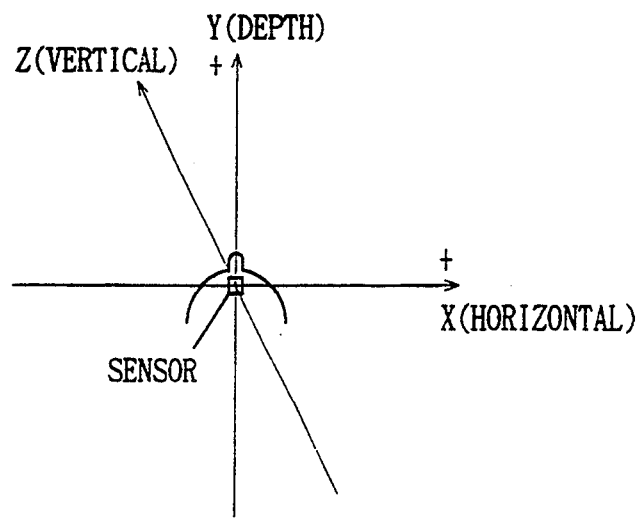
FIG. 21(a-b) shows a head coordinate system.
Figure 21:
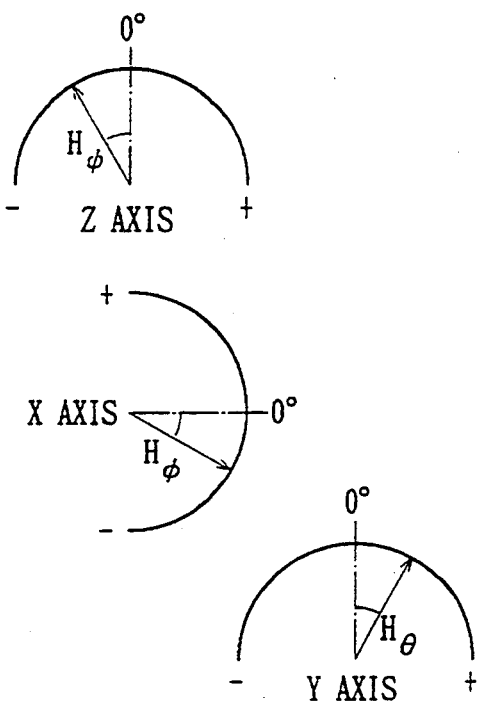

FIG. 21 is an illustration showing the principle of the head coordinate system with the subject being the center. Referring to FIG. 21, the head coordinate system detected by the head movement detecting portion 6 will be described. The head coordinate system includes two systems, that is, XY coordinate system realized by the translational movement of the subject with respect to the object of monitoring such as shown in FIG. 21(a), and a polar coordinate system based on the rotation movement of the head such as shown in FIG. 21(b). The amount of head movement in respective coordinate systems are defined as (Hx, Hy, Hz), (H$\psi$, H$\phi$, H$\theta$). In this embodiment, the direction toward the object of monitoring is represented by the Y axis, the horizontal movement is represented by the X axis and the vertical movement is represented by the Z axis, as an example. H$\varepsilon$ represents the rotation of the X axis, that is, the movement of one's neck upward or downward. H$\theta$ represents the rotation of the Y axis, that is, the movement of inclining ones neck once from the left shoulder to the right shoulder. H$\psi$ represents rotation in the Z axis, that is, rotation of one's neck in the left or right direction.

The line-of-sight changes by the horizontal movement of the head (Hx, Hy, Hz), and when this movement is changed in the equivalent of rotation angle of the eye ball (Ex, Ey), the following equations are obtained.

$$Ex = 180/\pi \cdot \tan^{-1} Hx/(D+Hy) \quad (1)$$

$$Ey = 180/\pi \cdot \tan^{-1} Hz/(D+Hy) \quad (2)$$

where D: distance from the subject to the point of gazing.

When the neck is inclined by H$\theta$ to the left shoulder or to the right shoulder, the coordinate of the eye movement system rotates. Therefore, the eye movement coordinate system (Xe, Ye) inclined by H$\theta$ must be changed to the coordinate system (Xe', Ye') which is orthogonal to the original object of monitoring.

$$Xe' = Xe \cdot \cos H\theta + Ye \cdot \sin H\theta \quad (3)$$

$$Ye' = -Xe \cdot \sin H\theta + Ye \cdot \cos H\theta \quad (4)$$

The movement of the line-of-sight (Xh, Yh) realized by the head movement is represented by the following equations (5) and (6) derived from the equations (1) and (2).

$$Xh = Ex + H\psi \quad (5)$$

$$Yh = Ey + H\phi \quad (6)$$

Therefore, the movement of the line-of-sight (Vx, Vy) taking the head movement into account is represented by the following equations (7) and (8), from equations (3) to (6).

$$Vx = Xe' + Xh \quad (7)$$

$$Vy = Ye' + Yh \quad (8)$$

By employing the equations (7) and (8) above, the ordinary movement of one's line-of-sight effected by combining head movement and eye movement can be reproduced.

Figure 22:
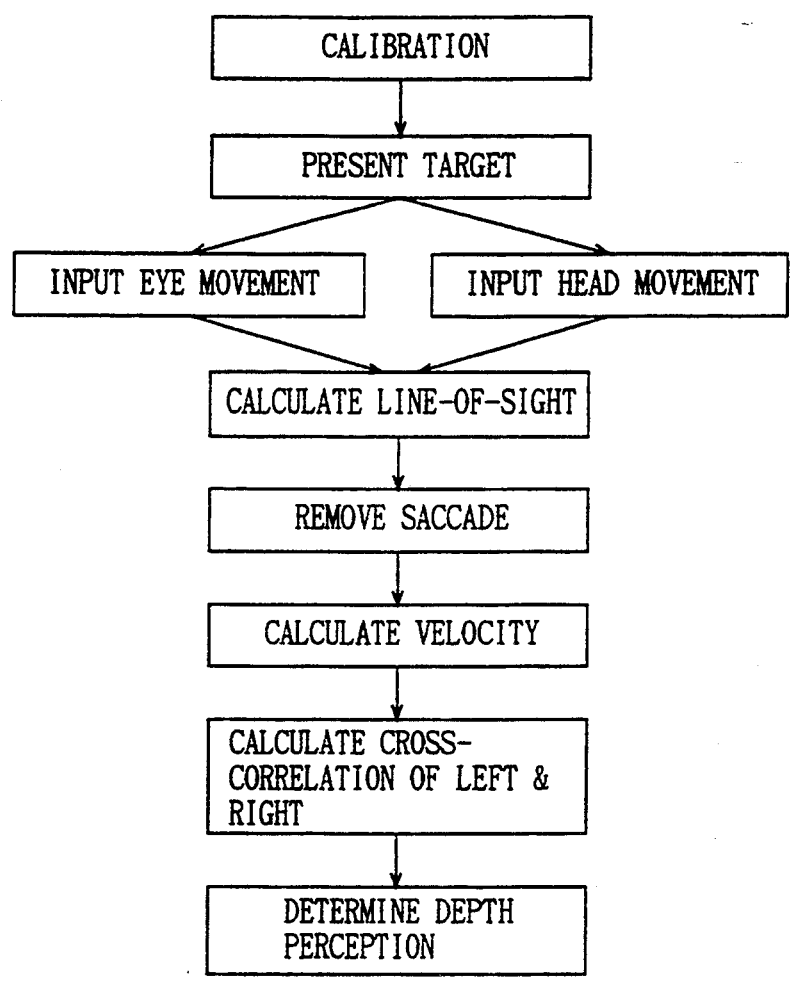
FIG. 22 is a flow chart showing the operation of a further embodiment of the present invention.

FIG. 22 is a flow chart showing the operation of another embodiment of the present invention. In this embodiment, calibration is done, and target is presented in the same manner as discussed above with reference to FIG. 7, the eye movement of the subject at that time is detected by the eye movement detecting portion 2, and the head movement of the subject is detected by the head movement detecting portion 6. The arithmetic operation portion 1 carries out the operations in accordance with the equations (1) to (8) on the basis of the detected head movement data and the eye movement data, and calculates parameters in the same manner as in the embodiment shown in FIG. 7. More specifically, in place of Xeye and Yeye in the embodiment shown in FIG. 7, analysis of depth perception is effected by using the movement of the line-of-sight Vx and Vy calculated in accordance with the equations (7) and (8). The method of analysis is the same as in the embodiment shown in FIG. 7.

As described above, according to the present embodiment, since the head movement is also detected, it is not necessary to fix the subject by using a chin rest as in the first embodiment to prevent the movement of the body of the subject disturbing the measurement of the position of the line-of-sight on the basis of the eye movement component. Therefore, measurement can be carried out while the subject can freely move his head. Therefore, burden on the subject is small, and measurement can be carried out easily. Therefore depth perception in the natural state can be determined.

As described above, according to the embodiment of the present invention, eye movement of both eyes of the subject when a target is presented to the subject for generating depth perception is detected, the saccade component is removed by using velocity or acceleration of the detected eye movement, the vergence eye movement only is extracted, amplitude and change in the vergence eye movement and cross-correlation of velocity and acceleration of the left and right eye movement are calculated to measure depth perception of the subject in objective manner in real time, and therefore the result of measurement can be utilized for evaluation of stereoscopic images.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An apparatus for analyzing depth perception of a subject, comprising:
   target presenting means for presenting a target for generating depth perception of said subject;
   eye movement detecting means for detecting movement of both eyes of said subject; and
   calculating means, coupled to said eye movement detecting means, for removing a saccade component by calculating velocity or acceleration of the eye movement detected by said eye movement detecting means, extracting only vergence eye movement and calculating an amplitude of said vergence eye movement, a change in convergence angle, and cross-correlation of velocity or acceleration of left and right eye movement to determine depth perception of said subject.

2. The apparatus for analyzing depth perception according to claim 1, further comprising:
   head movement detecting means for detecting head movement of said subject,
   wherein said calculating means further includes means responsive to the head movement detected by said head movement detecting means and to the eye movement detected by said eye movement detecting means for calculating amplitude of convergence eye movement, change in convergence angle, and cross-correlation of velocity or acceleration of left and right eye movement for determining depth perception of said subject.

3. The apparatus for analyzing depth perception according to claim 1, wherein
   said calculating means includes means for determining which of the left and right eyes of the subject move faster on the basis of the result of calculation of said cross-correlation.

4. The apparatus for analyzing depth perception according to claim 1, wherein:
   said target presenting means includes stereoscopic image presenting means for presenting a stereoscopic image to said subject, and
   image control means for generating disparity between both eyes by moving an image out of said stereoscopic image corresponding to one of the eyes, wherein
   said calculating means includes means for determining depth perception in response to detection output from said eye movement detecting means while said subject is gazing at said stereoscopic image.

5. The apparatus for analyzing depth perception according to claim 2, wherein said calculating means includes means for determining which of the left and right eyes of the subject move faster on the basis of the result of calculation of said cross-correlation.

6. The apparatus for analyzing depth perception according to claim 2, wherein said target presenting means includes stereoscopic image presenting means for presenting a stereoscopic image to said subject, and image control means for generating disparity between both eyes by moving an image out of said stereoscopic image corresponding to one of the eyes, wherein said calculating means includes means for determining depth perception in response to detection output from said eye movement detecting means while said subject is gazing at said stereoscopic image.

* * * * *